US009861685B2

(12) United States Patent
Zennadi

(10) Patent No.: US 9,861,685 B2
(45) Date of Patent: Jan. 9, 2018

(54) METHODS OF TREATING HEMOGLOBINOPATHIES

(71) Applicant: Duke University, Durham, NC (US)

(72) Inventor: Rahima Zennadi, Durham, NC (US)

(73) Assignee: Duke University, Durham, NC (US)

(*) Notice: Subject to any disclaimer, the term of this patent is extended or adjusted under 35 U.S.C. 154(b) by 0 days.

(21) Appl. No.: 14/646,284

(22) PCT Filed: Nov. 20, 2013

(86) PCT No.: PCT/US2013/070895
§ 371 (c)(1),
(2) Date: May 20, 2015

(87) PCT Pub. No.: WO2014/081760
PCT Pub. Date: May 30, 2014

(65) Prior Publication Data
US 2015/0265684 A1 Sep. 24, 2015

Related U.S. Application Data

(60) Provisional application No. 61/728,593, filed on Nov. 20, 2012.

(51) Int. Cl.
*A61K 39/395* (2006.01)
*A61K 38/45* (2006.01)
*G01N 33/80* (2006.01)
*C12N 9/12* (2006.01)
*C07K 16/18* (2006.01)
*C07K 16/40* (2006.01)
*C12N 15/113* (2010.01)
*G01N 33/50* (2006.01)

(52) U.S. Cl.
CPC .............. *A61K 38/45* (2013.01); *C07K 16/18* (2013.01); *C07K 16/40* (2013.01); *C12N 9/12* (2013.01); *C12N 15/1137* (2013.01); *C12N 15/1138* (2013.01); *C12Y 207/11* (2013.01); *C12Y 207/11015* (2013.01); *G01N 33/5091* (2013.01); *G01N 33/80* (2013.01); *C07K 2317/76* (2013.01); *C12N 2310/14* (2013.01); *G01N 2800/22* (2013.01)

(58) Field of Classification Search
CPC ...................................... A61K 38/40
See application file for complete search history.

(56) References Cited

U.S. PATENT DOCUMENTS

2001/0027215 A1 10/2001 Perrine
2007/0049591 A1 3/2007 Pinkerton et al.
2008/0057590 A1* 3/2008 Urdea ............... G01N 33/74
436/71
2009/0285786 A1 11/2009 Zon et al.
2010/0286178 A1 11/2010 Ibrahim et al.
2011/0293558 A1 12/2011 Suresh et al.
2014/0179700 A1 6/2014 Zennadi

FOREIGN PATENT DOCUMENTS

WO 02/076496 A1 10/2002
WO 02/102232 A2 12/2002
WO 12/149547 A1 11/2012
WO 2015/179855 11/2015

OTHER PUBLICATIONS

Elisabeth Kohne, Hemoglobinopathies: Clinical Manifestations, Diagnosis, and Treatment https://www.ncbi.nlm.nih.gov/pmc/articles/PMC3163784/#s3title Dtsch Arztebl Int. Aug. 2011; 108(31-32): 532-540. Published online Aug. 8, 2011. doi: 10.3238/arztebl.2011.0532.*
http://www.stedmansonline.com/content.aspx?id=mlrS0900000600&termtype=t Accessed Jan. 6, 2017.*
http://www.stedmansonline.com/content.aspx?id=mlrH0500006672&termtype=t Accessed Jan. 6, 2017.*
http://www.stedmansonline.com/content.aspx?id=mlrT0800000239&termtype=t Accessed Jan. 6, 2017.*
Ballas, S.K. et al., "Red blood cell changes during the evolution of the sickle cell painful crisis," Blood 1992, 79:2154-2163.
Belcher J.D. et al., "Activated monocytes in sickle cell disease: potential role in the activation of vascular endothelium and vaso-occlusion," Blood 2000, 96:2451-2459.
Brunati A.M. at al., "Sequential phosphorylation of protein band 3 by Syk and Lyn tyrosine kinases in intact human erythrocytes: identification of primary and secondary phosphorylation sites," Blood 2000, 96:1550-1557.
Brzostowski J.A. et al., G-protein-independent functions for 7-TM receptors, Trends Biochem Sci 2001, 26:291-297.
Crews C.M., et al. "Their fifteen minutes has arrived," Cell Growth Differ 1992, 3:135-142.
Fincham V.J. et al., "Active ERK/MAP kinase is targeted to newly forming cell-matrix adhesions by integrin engagement and v-Src," EMBO J 2000, 19:2911-2923.
Frenette P.S. et al., Sickle cell disease: old discoveries, new concepts, and future promise, J Clin Invest 2007, 117:850-858.
George A. et al., "Altered phosphorylation of cytoskeleton proteins in sickle red blood cells: the role of protein kinase C, Rac GTPases, and reactive oxygen species," Blood Cells Mol Dis 2010, 45:41-45.
Hebbel, R.P. et al., "Erythrocyte adherence to endothelium in sickle-cell anemia: A possible determinant of disease severity," N Engl J Med 1980, 302:992-995.
Hines, P.C. et al., "Novel epinephrine and cyclic AMP-mediated activation of BCAM/Lu-dependent sickle (SS) RBC adhesion," Blood 2003, 101:3281-3287.
Houslay MD. et al., "Cell-type specific integration of cross-talk between extracellular signal-regulated kinase and cAMP signaling," Mol Pharmacol 2000, 58:659-668.

(Continued)

*Primary Examiner* — Gyan Chandra
(74) *Attorney, Agent, or Firm* — Andrus Intellectual Property Law, LLP

(57) ABSTRACT

Methods of alleviating the symptoms of hemoglobinopathies, including, but not limited to, sickle cell disease, β-thalassemia, and hemoglobin H disease are provided. In some embodiments, the methods comprise administering an inhibitor selected from a β-arrestin1/2 inhibitor and/or a GRK2 inhibitor to the subject. Methods of inhibiting adhesion of sickle red blood cells to endothelial cells and adhesion to and activation of leukocytes are also provided.

10 Claims, 6 Drawing Sheets

(56) References Cited

OTHER PUBLICATIONS

Jindal H.K. et al., "Specific loss of protein kinase activities in senescent erythrocytes," Blood 1996, 88:1479-1487.
Kaul D.K. et al., "Vaso-occlusion by sickle cells: evidence for selective trapping of dense red cells," Blood 1986, 68:1162-116.
Kaul, D.K. et al. "Adhesion of sickle cells to vascular endothelium is critically dependent on changes in density and shape of the cells," Blood 1994, 83:3006-3017.
Koch, W.J. et al., "Direct evidence that Gi-coupled receptor stimulation of mitogen-activated protein kinase is mediated by Gβγ activation of p21ras," (1994) Proc Natl Acad Sci USA 91:12706-112710.
Laubach, J.P. et al., "Polycythemia vera erythroid precursors exhibit increased proliferation and apoptosis resistance associated with abnormal RAS and PI3K pathway activation," (2009) Experimental Hematology 37:1411-1422.
McElveen, R.L. et al., "Erk pathway inhibitor U0126 induces gamma-globin expression in erythroid cells," (2005) Cell Mol Biol (Noisy-le-grand) 51(2):215-227.
Mohandas, N. et al. "Sickle erythrocyte adherence to vascular endothelium. Morphologic correlates and the requirement for divalent cations and collagen-binding plasma proteins," J Clin Invest 1985, 76:1605-1612.
Nagata, Y. et al., "Requirement of activation of JNK and p38 for environmental stress-induced erythroid differentiation and apoptosis and of inhibition of ERK for apoptosis," (1999) Blood 94(3):853-863.
Platt O.S. et al., "Mortality in sickle cell disease. Life expectancy and risk factors for early death," N Engl J Med 1994, 330:1639-44.
Polanowska-Grabowska, R. et al., "P-Selectin-mediated platelet-neutrophil aggregate formation activates neutrophils in mouse and human sickle cell disease," (2010) Arteriosclerosis, Thrombosis, and Vascular Biology 30:2392-2399.
Rengo, G. et al., "GRK2 as a novel gene therapy target in heart failure," (2011) J. Mol Cell Cardiol 50(5):785-792.
Schmidt E.K. et al., "PI3 kinase is important for Ras, MEK and Erk activation of Epo-stimulated human erythroid progenitors," BMC Biol 2004, 2:7.
Schmitt, J.M. et al., "beta 2-adrenergic receptor activates extracellular signal-regulated kinases (ERKs) via the small G protein rap1 and the serine/threonine kinase B-Raf," J Biol Chem 2000, 275:25342-25350.
Selvaraj, S. K. et al., "Mechanisms of monocyte activation and expression of proinflammatory cytochemokines by placenta growth factor," (2003) Blood 102:1515-1524; prepublished online Apr. 10, 2003.
Serjeant, G.R., "Sickle-cell disease," (1997) The Lancet 350:725-730.
Soderblom, E. et al., "Proteomic analysis of ERK1/2-mediated human sickle red blood cell membrane protein phosphorylation," (2013) Clinical Proteomics 10:1-16.
Turhan A. et al., "Primary role for adherent leukocytes in sickle cell vascular occlusion: a new paradigm," Proc Natl Acad Sci U S A 2002, 99:3047-3051.
Udani M. et al., "Basal cell adhesion molecule/lutheran protein. The receptor critical for sickle cell adhesion to laminin," J Clin Invest 1998, 101:2550-2558.
Wannatung, T. et al., "Increased erythropoiesis of β-thalassaemia/ Hb E proerythroblasts is mediated by high basal levels of ERK1/2 activation," (2009) British J. of Haematology 146:557-568.
Zambuzzi, W.F. et al., "On the road to understanding of the osteoblast adhesion: cytoskeleton organization is rearranged by distinct signaling pathways," J Cell Biochem 2009, 108:134-144.
Zennadi R., et al., "Sickle red cells induce adhesion of lymphocytes and monocytes to endothelium," Blood 2008, 112:3474-3483.
Zennadi, R. et al., Atypical activation of plasma membrane-bound ERK1/2 is associated with regulation of sickle red cell adhesion to endothelium, Dec. 6, 2010, Retrieved from the Internet: https://ash.confex.com/ash/2010/webprogram/Paper33039.html (Abstract).
Zennadi, R. et al., "Epinephrine acts through erythroid signaling pathways to activate sickle cell adhesion to endothelium via LW-alphavbeta3 interactions," Blood 2004, 104:3774-3781.
Zennadi, R. et al., "Epinephrine-induced activation of LW-mediated sickle cell adhesion and vaso-occlusion in vivo," Blood 2007, 110:2708-2717.
Zennadi, R. et al., "Erythrocyte plasma membrane-bound ERK1/2 activation promotes ICAM-4-mediated sickle red cell adhesion to endothelium," (2012) Blood 119(5):1217-1227; prepublished online as Blood First Edition paper, Dec. 6, 2011.
Zennadi, R., "MEK inhibitors, novel anti-adhesive molecules, reduce sickle red blood cell adhesion in vitro and in vivo, and vasoocclusion in vivo," (2014) PloS ONE 9(10): e110306. doi:10.1371/journal.pone.0110306.
International Search Report and Written Opinion for International Application No. PCT/US2012/035837 dated Aug. 16, 2012 (16 pages).
International Search Report and Written Opinion for International Application No. PCT/US2013/070895 dated Jan. 17, 2014 (10 pages).
European Search Report for European Patent Application No. EP12775962.9 dated Sep. 4, 2014 (18 pages).
International Search Report and Written Opinion for International Patent Application PCT/US2015/032366 dated Aug. 12, 2015.
Zhao, et al., "MEK1/2 inhibitors reverse acute vascular occlusion in mouse models of sickle cell disease," (2016) FASEB J 30: 1171-1186.

\* cited by examiner

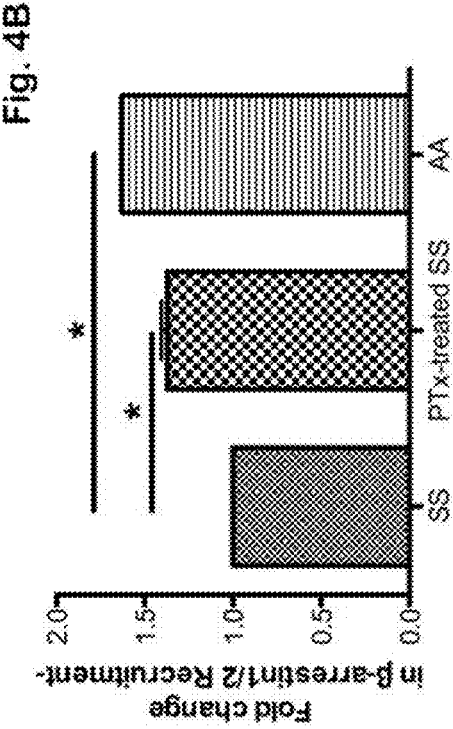
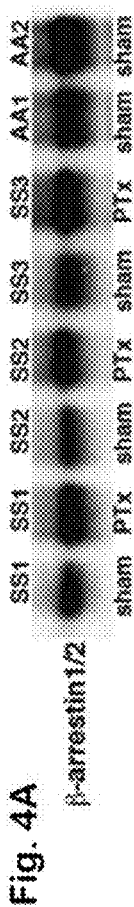
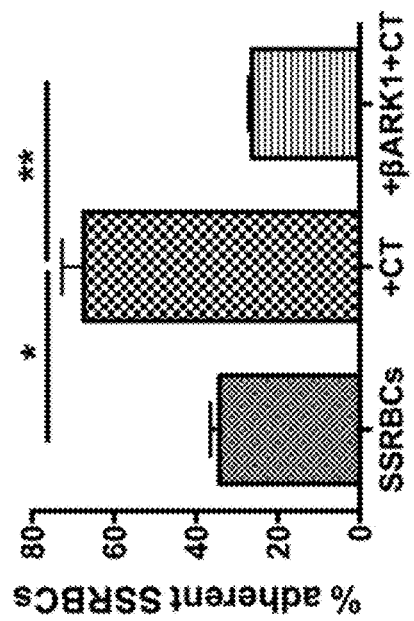

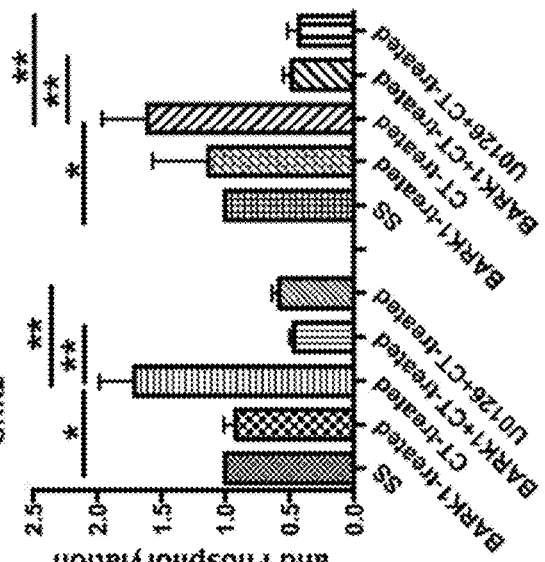
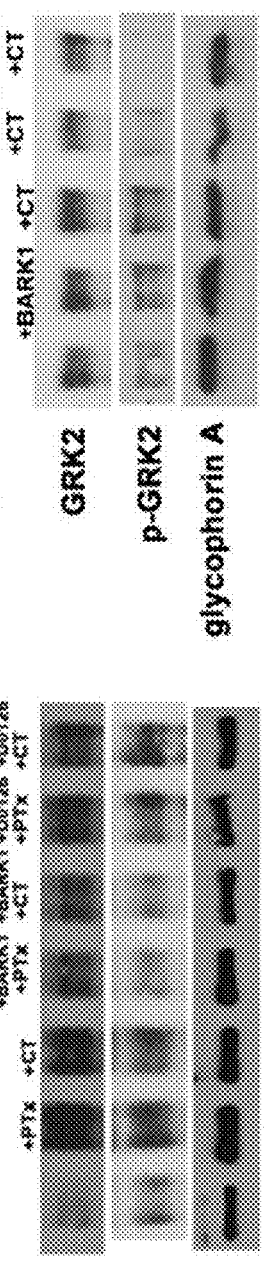
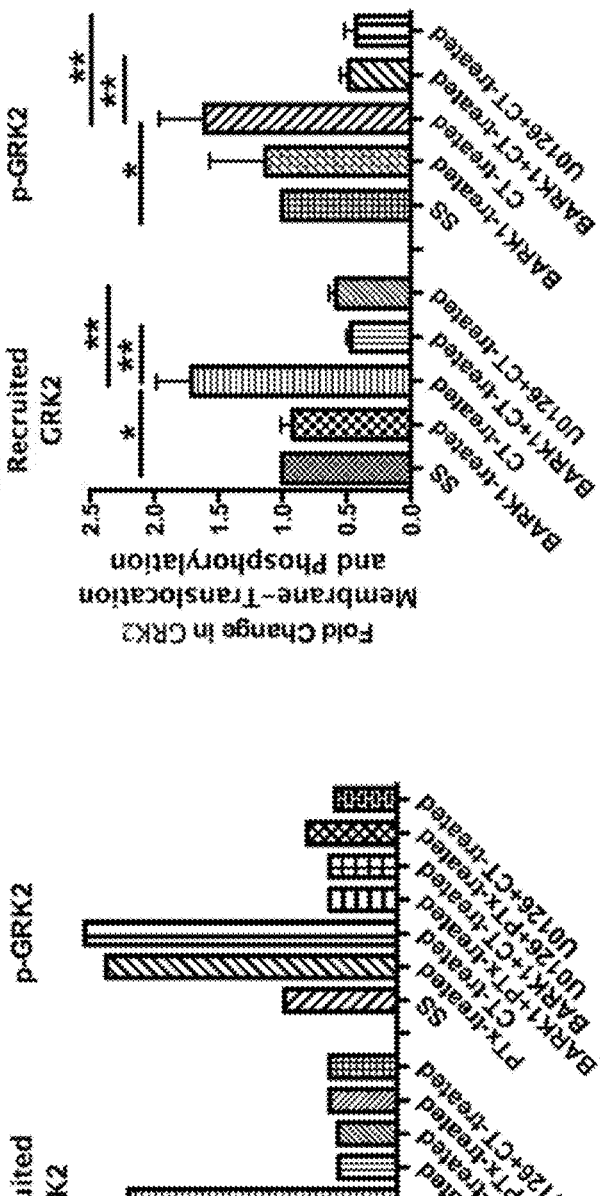

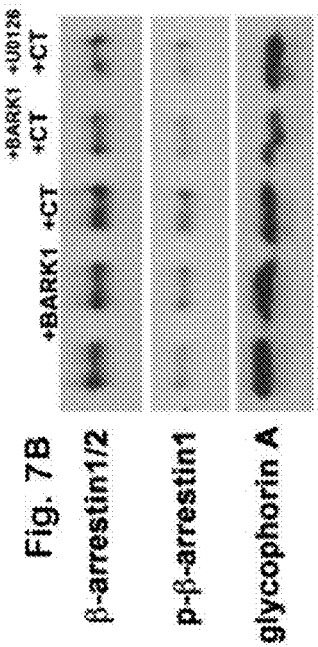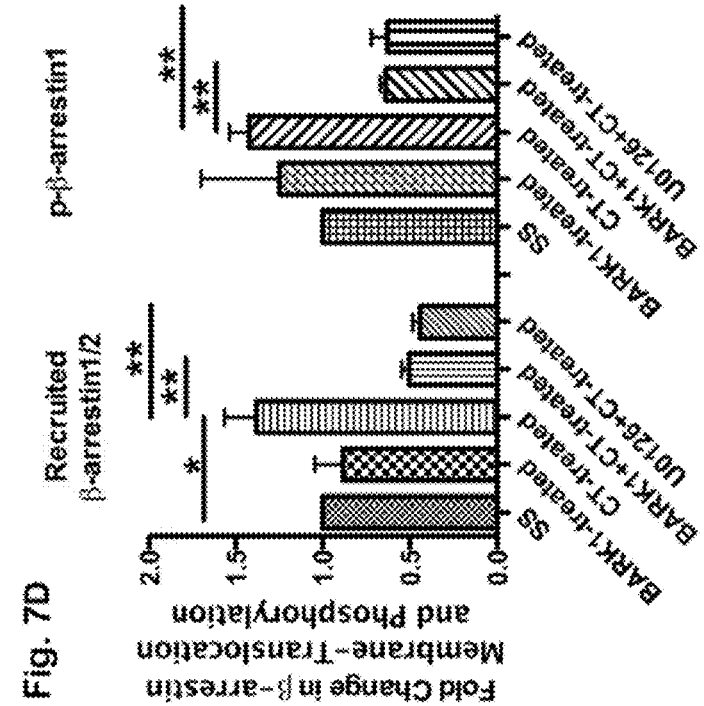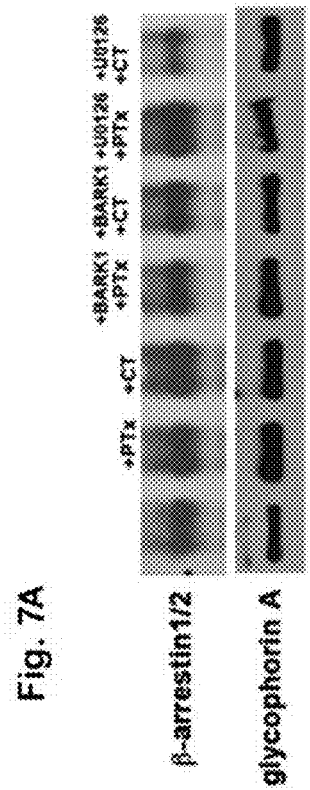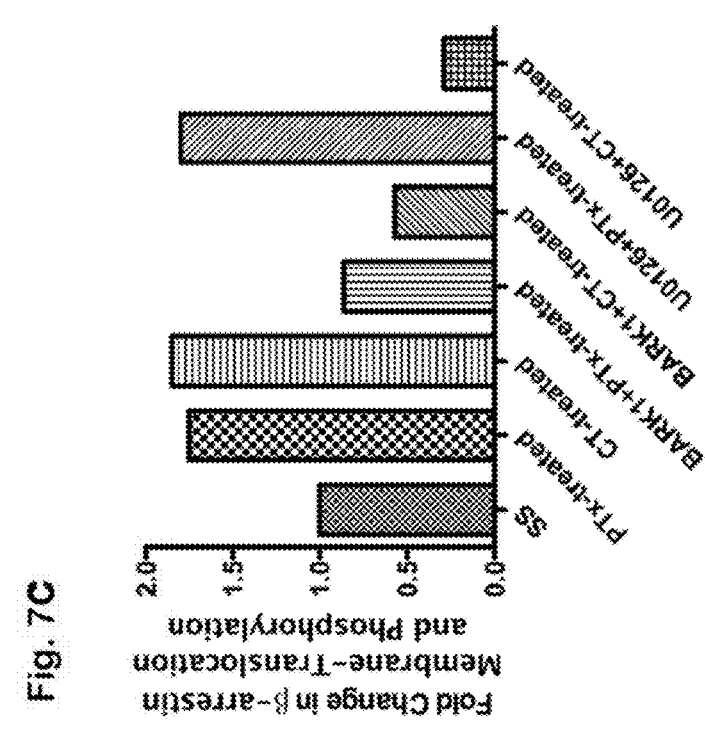
Fig. 7A
Fig. 7B
Fig. 7C
Fig. 7D

METHODS OF TREATING HEMOGLOBINOPATHIES

CROSS-REFERENCE TO RELATED APPLICATIONS

This patent application is a national stage filing under 35 U.S.C. 371 of International Application No. PCT/US2013/070895, filed Nov. 20, 2013, which claims the benefit of priority of U.S. Provisional Patent Application No. 61/728,593, filed Nov. 20, 2012, both of which are incorporated herein by reference in their entirety.

STATEMENT REGARDING FEDERALLY SPONSORED RESEARCH

This invention was made with government support under K01-DK065040 awarded by the National Institutes of Health: National Institute of Diabetes and Digestive and Kidney Diseases. The government has certain rights in the invention.

BACKGROUND

Vaso-occlusive phenomena and hemolytic anemia are the clinical hallmarks of sickle cell disease (SCD). Sickle (homozygous hemoglobin S, SS) red blood cell (RBC)-based adhesion and vaso-occlusive events likely initiate and/or exacerbate the profound vasculopathy present in SCD.[1, 2] SS RBCs possess unusually active signaling pathways that contribute to a panoply of abnormalities, including RBC adhesion to the endothelium and vaso-occlusion.[2-4] Vaso-occlusion results in recurrent painful episodes and a variety of serious organ system complications that can lead to life-long disabilities and even death.

Cell adhesion is a multistep cellular process that is regulated by complex extracellular and intracellular signals, which may differ from one cell type to another. We have previously shown that abnormal SS RBC interaction with the endothelium and with leukocytes can be increased via stimulation of $\beta_2$ adrenergic receptors (ARs) by the stress hormone epinephrine.[4-6] Such stimulation activates the intracellular cyclic adenosine monophosphate (cAMP)/protein kinase A (PKA) pathway.[4] βARs are prototypic G protein-coupled receptors (GPCRs), whose signaling properties are largely mediated by activation of stimulatory GTP-binding proteins (Gs proteins), which in turn activate adenylate cyclase (AC), leading to generation of cAMP, and the subsequent activation of PKA. The cAMP/PKA pathway can modulate the mitogen-activated protein kinase (MAPK)/extracellular signal-regulated kinase (ERKs) cascade.[7] PKA has been reported to stimulate B-Raf, while inhibiting c-Raf. Therefore, the activity of downstream signaling proteins, such as MEKs and ERKs, could be either enhanced or inhibited depending on the balance of c-Raf and B-Raf activation.[8, 9] The cellular functions mediated by βARs can also be independent of adenylyl cyclase activation and involve other mediators instead.[10, 11]

We recently demonstrated that MEK/ERK inhibitors are capable of alleviating the symptoms associated with hemoglobinopathy in subjects afflicted therewith. It would be advantageous to target further potential pathways and uncover further inhibitors to treat or block these symptoms.

SUMMARY

In some embodiments, methods of alleviating at least one symptom of a hemoglobinopathy in a subject are provided. In some embodiments, a hemoglobinopathy is selected from sickle cell disease, β-thalassemia, and hemoglobin H disease. In some embodiments, a hemoglobinopathy is sickle cell disease. In some embodiments, at least one symptom is selected from vaso-occlusion, acute or chronic painful episodes, chronic hemolysis (aplastic crises), avascular necrosis, infection, end-organ damage, and erythroid hyperplasia.

In some embodiments, methods of inhibiting adhesion of sickle red blood cells to endothelial cells in a subject are provided. In some embodiments, methods of inhibiting adhesion of sickle red blood cells to leukocytes in a subject are provided. The sickle red blood cells interact with leukocytes and activate them increasing adhesion of the leukocytes to other cells as well. In some embodiments, methods of inhibiting formation of multicellular aggregates in a subject with sickle cell disease are provided. In some embodiments, methods of inhibiting sickle red blood cell-induced activation and adhesion of leukocytes to endothelial cells in a subject with sickle cell disease are provided.

In some embodiments, a method comprises administering at least one inhibitor selected from a β-arrestin1/2 inhibitor and a GRK2 inhibitor to the subject.

In some embodiments, the inhibitor is a siRNA, an antibody or a small molecule inhibitor of β-arrestin1/2 or GRK2.

In some embodiments, a method of inhibiting adhesion of sickle red blood cells to endothelial cells is provided. In some embodiments, a method of inhibiting adhesion of sickle red blood cells to leukocytes is provided. In some embodiments, a method of inhibiting formation of multicellular aggregates in the presence of sickle red blood cells is provided. In some embodiments, a method of inhibiting adhesion of leukocytes to endothelial cells in the presence of sickle red blood cells is provided.

In some embodiments, a method comprises contacting sickle red blood cells with an inhibitor selected from a β-arrestin1/2 inhibitor and a GRK2 inhibitor to the subject.

In some embodiments, the inhibitor is a siRNA, an antibody or a small molecule inhibitor of β-arrestin1/2 or GRK2.

In a further aspect, methods of determining the severity of sickle cell disease are provided. The methods include obtaining a blood sample including red blood cells from a subject and optionally treating the red blood cells with at least one of cholera toxin, pertussis toxin or epinephrine. The cells are then assessed for at least one of ERK phosphorylation, GRK2 membrane translocation and phosphorylation, or β-arrestin1/2 membrane translocation and phosphorylation. The level of ERK phosphorylation, GRK2 membrane translocation and phosphorylation, or β-arrestin1/2 membrane translocation and phosphorylation is related to the severity of sickle cell disease and/or the likelihood of the red blood cells to adhere to other cells.

B. Quantitative analysis of the data (normalized according to glycophorin C expression) is presented as fold change in β-arrestin and GRK2 membrane-recruitment and phosphorylation. β-arrestin1/2 and GRK2 are expressed in SSRBCs. Treatment of SSRBCs with PTx, CT or Epi increased the amounts of β-arrestin1/2 and GRK2 bound to the membrane compared with the amounts of β-arrestin1/2 and GRK2 bound to the membrane of sham-treated SSRBCs, indicating an increase in recruitment of both β-arrestin1/2 and GRK2 from the cytoplasm to the membrane. GRK2 is slightly phosphorylated at baseline, and its phosphorylation increased as a result of SSRBC treatment with PTx, CT or Epi. Similarly, β-arrestin1 is also slightly phosphorylated at baseline, and its phosphorylation increased as a result of SSRBC treatment with CT or Epi. *: $p<0.05$ compared to SSRBCs. Error bars show SEM of 3 different experiments.

Figure 2:
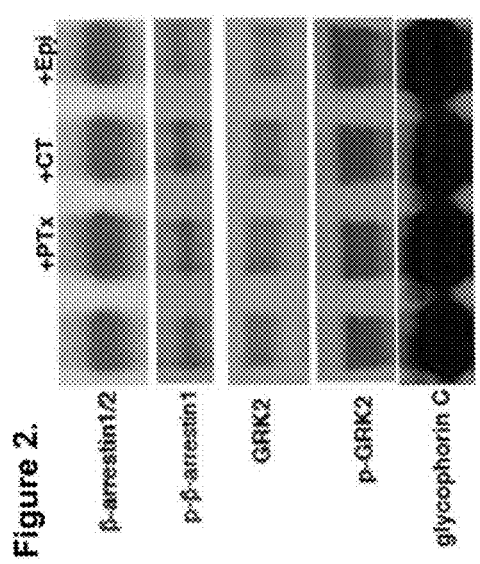

FIG. 2. Membrane-translocation of β-arrestin1/2 and GRK2 does not occur in normal RBCS. Normal (AA) RBCs (n=4) were sham-treated, or treated with 2 μg/ml Pertussis toxin (PTx) for 30 min; 2 μg/ml Cholera toxin (CT) for 10 min; or 20 nM epinephrine (Epi) for 1 min. Forty μg of membrane protein ghosts were used per lane. RBC membrane protein ghosts were blotted for the total amounts of β-arrestin1/2 and GRK2, and for phosphorylated β-arrestin1 and phosphorylated GRK2. An anti-glycophorin C antibody is used as a loading control. β-arrestin1/2 and GRK2 are expressed in AARBCs, and treatment of AARBCs with PTx, CT or Epi failed to increase the amounts of β-arrestin1/2 and GRK2 bound to the plasma membrane compared with the amounts of β-arrestin1/2 and GRK2 bound to the membrane of sham-treated AARBCs ($p>0.05$). GRK2 and β-arrestin1 are phosphorylated at baseline, and these two kinases did not undergo increased phosphorylation as a result of cell stimulation with PTx, CT or Epi ($p>0.05$).

Figures 3, 3A:
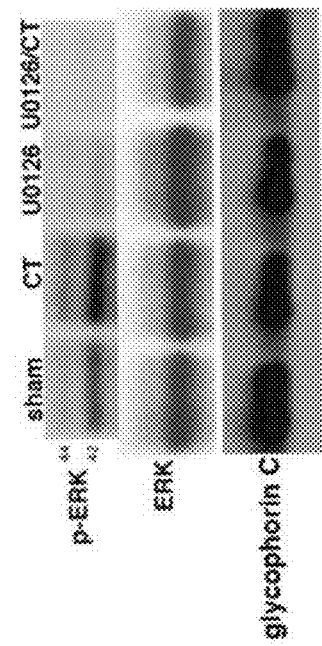

FIG. 3. ERK phosphorylation is $G\alpha_s$ protein-dependent. SSRBCs (n=3) were sham-treated, or treated with 10 μM U0126 for 1 h; 2 μg/ml Cholera toxin (CT) for 10 min; or 10 μM MEK inhibitor U0126, which selectively inhibits ERK, for 1 h followed by 2 μg/ml CT for 10 min. Forty μg of membrane protein ghosts were used per lane. A. RBC membrane protein ghosts were blotted for phosphorylated ERK and total ERK. An anti-glycophorin C antibody is used as a loading control. B. Quantitative analysis of the data (normalized according to glycophorin C expression) is presented as fold change in ERK phosphorylation. ERK is expressed in SSRBCs, is bound to the RBC plasma membrane and is slightly phosphorylated at baseline. ERK undergoes increased phosphorylation after RBC incubation with CT, which is inhibited by U0126. *: $p<0.05$ compared to SSRBCs, and **: $p<0.001$ compared to CT-treated. Error bars show SEM of 3 different experiments.

FIG. 4. The amounts of β-arrestin1/2 membrane-bound in normal RBCs are much higher than in SSRBCs. Normal (AA) RBCs were sham-treated, and SSRBCs were sham-treated or treated with 2 μg/ml Pertussis toxin (PTx) for 30 min. A. Forty μg of membrane protein ghosts were used per lane. Western blots were stained with the antibody against β-arrestin1/2. B. Quantitative analysis of the data is presented as fold change in β-arrestin1/2 recruitment. The amounts of membrane-bound β-arrestin1/2 in AARBCs (n=2) were significantly higher than in SSRBCs (n=3). PTx treatment of SSRBCs induced membrane-recruitment of β-arrestin1/2, which resulted in increased amounts of membrane-bound β-arrestin1/2. *: $p<0.0001$ compared to SSRBCs.

FIG. 5. GRK2 is involved in SSRBC adhesion to normal-endothelial cells in vitro. Adhesion of SSRBCs to non-activated human umbilical vein endothelial cells (HUVECs) was tested in intermittent flow condition assays, and results are presented as % adherent SSRBCs at a shear stress of 2 dynes/cm$^2$. SSRBCs were sham-treated, or treated with 2 μg/ml Cholera toxin (CT) for 10 min, or 10 μM GRK2 inhibitor βARK1 for 1 h followed by 2 μg/ml CT for 10 min. CT significantly up-regulated SSRBC adherence to non-treated HUVECs. However, the effect of CT on SSRBC adhesion to HUVECs was significantly inhibited with the GRK2 inhibitor βARK1. *: $p<0.05$ compared to non-treated SSRBC adherence to non-activated HUVECs; **: $p<0.05$ compared to CT-treated SSRBCs adherent to non-activated HUVECs. Error bars show SEM of 3 different experiments.

FIG. 6. Membrane-translocation and phosphorylation of GRK2 are triggered by ERK activation. SSRBCs (n=5) were sham-treated, or treated with 2 μg/ml PTx for 30 min; 2 μg/ml CT for 10 min; 10 μM GRK2 inhibitor βARK1 for 1 h; 10 μM GRK2 inhibitor βARK1 for 1 h followed by 2 μg/ml PTx for 30 min; 10 μM GRK2 inhibitor βARK1 for 1 h followed by 2 μg/ml CT for 10 min; 10 μM MEK inhibitor U0126 for 1 h followed by 2 μg/ml PTx for 30 min; or 10 μM MEK inhibitor U0126 for 1 h followed by 2 μg/ml CT for 10 min. Forty μg of membrane protein ghosts were used per lane. A and B. Protein membrane ghosts were blotted for the total amounts of GRK2, and for phosphorylated GRK2. An anti-glycophorin A antibody is used as a loading control. C and D. Quantitative analysis of the data presented in panels A and B, respectively, (normalized according to glycophorin A expression) is presented as fold change in GRK2 membrane-recruitment and phosphorylation. Treatment of SSRBCs with PTx or CT increased the amounts of GRK2 bound to the membrane compared with the amounts of GRK2 bound to the membrane of sham-treated SSRBCs, indicating an increase in recruitment of GRK2 from the cytoplasm to the membrane via Gs protein activation. GRK2 is phosphorylated to some degree at baseline, and its phosphorylation increased as a result of SSRBC treatment with PTx or CT. However, as expected, pre-treatment of SSRBCs with βARK1 significantly inhibited the effects of CT or PTx on GRK2 membrane-translocation and its phosphorylation. Pre-treatment of SSRBCs with the MEK inhibitor U0126 also significantly abrogated the action of CT and PTx on GRK2 membrane recruitment and phosphorylation, suggesting that ERK activation in SSRBCs both triggers GRK2 to translocate to the cytoplasmic membrane and contributes to its activation. *: $p<0.05$ compared to SSRBCs; and **: $p<0.001$ compared to CT-treated SSRBCs. Error bars show SEM of 5 different experiments.

FIG. 7. Membrane-translocation of β-arrestin1/2 and phosphorylation of β-arrestin1/2 are triggered by ERK activation and GRK2 recruitment to the cytoplasmic membrane. SSRBCs (n=5) were sham-treated, or treated with 2 μg/ml PTx for 30 min; 2 μg/ml CT for 10 min; 10 μM GRK2 inhibitor βARK1 for 1 h; 10 μM GRK2 inhibitor βARK1 for 1 h followed by 2 μg/ml PTx for 30 min; 10 μM GRK2 inhibitor βARK1 for 1 h followed by 2 μg/ml CT for 10 min; 10 μM MEK inhibitor U0126 for 1 h followed by 2 μg/ml PTx for 30 min; or 10 μM MEK inhibitor U0126 for 1 h followed by 2 μg/ml CT for 10 min. Forty μg of membrane protein ghosts were used per lane. A and B. Protein membrane ghosts were blotted for the total amounts of β-arrestin1/2, and for phosphorylated β-arrestin1. An anti-glycophorin A antibody is used as a loading control. C and D. Quantitative analysis of the data presented in panels A and B, respectively, (normalized according to glycophorin A expression) is presented as fold change in β-arrestin membrane-recruitment and phosphorylation. Treatment of SSRBCs with CT increased the amounts of β-arrestin1/2 bound to the membrane compared with the amounts of β-arrestin1/2 bound to the membrane of sham-treated SSRBCs, indicating an increase in recruitment of β-arrestin1/2 from the cytoplasm to the membrane via activation of Gs protein. PTx treatment had a non-significant effect on β-arrestin1/2 translocation to the membrane of SSRBCs in the sickle red blood samples tested. β-arrestin1 is phosphorylated slightly at baseline, and its phosphorylation increased, but not significantly, by CT treatment. However, pre-treatment of SSRBCs with either βARK1 or U0126 significantly inhibited the effects of CT on β-arrestin1/2 membrane-translocation and decreased the levels of β-arrestin1 phosphorylation, suggesting that ERK and GRK2 promote membrane recruitment of β-arrestin1/2 and activation of β-arrestin1. *: $p<0.05$ compared to SSRBCs; and **: $p<0.001$ compared to CT-treated SSRBCs. Error bars show SEM of 5 different experiments.

Figures 8A, 8B:
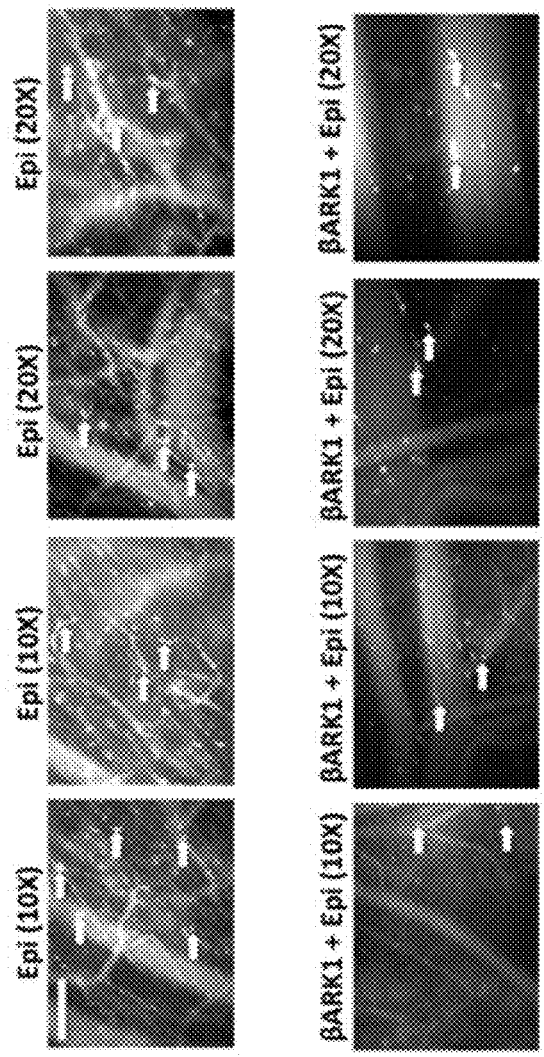

FIG. 8. GRK2 contributes to SSRBC adhesion to the vascular endothelium and vaso-occlusion in vivo. Human sickle RBCs were treated with epinephrine or the GRK2 inhibitor βARK1 followed by epinephrine ex vivo, washed extensively, and then infused into the tall vein of nude mice. Microscopic observations of venules were conducted through a dorsal skin-fold window chamber implant using 10× and 20× magnifications, after infusion of fluorescently labeled treated human SS RBCs. Vessels without adherent cells appear gray, due to rapidly moving fluorescent RBCs. FIG. 8A. Infusion of epinephrine-treated SS RBCs (n=2) resulted in marked RBC adherence in inflamed venules and vaso-occlusion as shown by arrows. FIG. 8B. Inhibition of the effect of epinephrine on SS RBCs with the GRK2 inhibitor βARK1 (n=2) shows rare adhesion in inflamed vessels as indicated by arrows, but no apparent vaso-occlusion. Scale bar=50 μm.

DETAILED DESCRIPTION

Effective therapies are desperately needed in sickle cell disease (SCD) to prevent and curtail the recurrent painful vaso-occlusive crises that lead to the multi-organ damage, an inevitable consequence of this disease. Current treatments for SCD achieve only symptomatic relief and have no demonstrated efficacy in preventing organ damage. Therapies that focus on ameliorating sickle red blood cell (RBC) dehydration[12-15], interfering with chemical-physical processes during erythrocyte-endothelial adhesion events[17], or targeting RBC adhesion molecules[4, 18, 19], to prevent RBC-endothelial cell interactions have shown little to no therapeutic benefit. While it is known that the abnormal sickle cell adhesion is the proximate cause of events that precipitate vaso-occlusion, there has been no attempt to target the signaling mechanisms required for sickle cell adhesion. The current major limitation in developing therapeutics for vaso-occlusive crises is our poor understanding of the specific signaling mechanisms that lead to increased sickle cell adhesion to endothelium, the subsequent stimulation of leukocyte adhesion, and the formation of vaso-occlusive cell aggregates. An in-depth understanding of sickle cell signaling pathways that mediate adhesion at both the biochemical and physiological levels will be required to successfully exploit these pathways for therapeutic purposes and to develop efficacious pathway-selective drugs with minimal side effects.

Earlier the present inventor suggested that the mitogen-activated protein kinase (MAPK)/the extracellular signal-regulated kinase (ERK1/2) is present at higher abundance in sickle red blood cells (SS RBCs) than in normal RBCs and is bound to the cytoplasmic membrane.[20] The present inventors have shown that ERK1/2 is active in enucleated SS RBCs, and that triggering this kinase promotes activation of signaling pathways and consequent RBC adhesion to the endothelium.[20] Stimulation of $β_2$ adrenergic receptors ($β_2$ARs) on SS RBCs by epinephrine for a brief period of time increases activation of the ERK1/2 signaling cascade, which is involved in phosphorylation of the RBC adhesion receptor ICAM-4. The present inventors also found that the ERK consensus motifs on dematin and α- and β-adducins undergo increased serine phosphorylation, indicating that these cytoskeletal proteins are substrates for ERK.

ERK has been implicated in EPO-induced erythroid cell proliferation and survival,[21] and the present inventors have now demonstrated that the activity of this kinase and its upstream signal are conserved in mature SS RBCs, and can be increased by either epinephrine or EPO. In some instances, ERK1/2 is hyperactive without stimulation of SS RBCs, and increased activation of this kinase can increase within 1 minute of SS RBC exposure to epinephrine. In contrast, in normal RBCs, despite the abundance of ERK1/2, ERK is not active at baseline and fails to become phosphorylated/activated with epinephrine or forskolin stimulation. See International Application Publication No. WO 2012/149547, which is incorporated herein by reference in its entirety. The inability of ERK1/2 to undergo activation in normal RBCs suggests that the activity of ERK itself and/or at least one of the upstream effectors required for ERK activation is lost. Indeed, investigators have previously described that RBCs undergo maturation-related loss of multiple protein kinase activities, including PKA, PKC, and casein kinases.[22] In contrast, although SS RBCs are also fully differentiated, the present inventors have found that preservation of ERK activity and its downstream signaling molecules appears to be involved at least in the abnormal activation of RBC adhesive function.

Our data further implicate involvement of the protein $G_s$ and cAMP/PKA as upstream mediators in activation of ERK and its downstream signal transduction pathway. Our findings are consistent with studies by Schmitt and Stork[7] demonstrating that isoproterenol stimulation of endogenous $β_2$ARs activated ERK in HEK293 cells via a cAMP-dependent PKA pathway, and ERK activation increased by treatment with PTx, which inactivates the protein $Gα_i$. In addition to PKA, we have also identified a role for the tyrosine kinase p72$^{Syk}$ in activation of ERK in SS RBCs, while excluding involvement of p56$^{lck}$-related Src family tyrosine kinases. Thus, in SS RBCs, PKA and the tyrosine kinase p72$^{Syk}$ are implicated in ERK activation, acting most likely in concert to regulate the MEK/ERK signaling pathway.

The engagement of epinephrine in regulation of SS RBC adhesion to the endothelium suggests that the MEK/ERK signal can promote an adhesive, vaso-occlusive pathology. Epinephrine-induced adhesion of SS RBCs to non-activated endothelial cells requires ICAM-4 phosphorylation, which occurs via the cAMP/PKA/MEK/ERK signaling pathway. Furthermore, the adhesive function of SS RBCs appeared to be related to the extent of ERK phosphorylation/activation, since both increased or decreased similarly depending on the time of cell exposure to epinephrine. Additionally, basal cAMP levels, the upstream effector of MEK/ERK, were much higher in SS RBCs than in normal cells, suggesting that the increased level of cAMP in SS RBCs reflects at least in part the persistence of the abnormal ERK activation and RBC adhesive phenotype. However, although epinephrine increased cAMP levels in only 50% of the SCD patient samples tested, cAMP production, which seems to be needed to activate ERK signaling in these sickle cells, was also influenced by the duration of cell exposure to epinephrine. This may be explained at least in part by the dramatic decrease in the abundance of phosphopeptides within CAP1 in SS RBCs due to continued cell exposure to epinephrine stimulation. PKA might also exert a negative feedback loop through activation of phosphodiesterases, resulting in cAMP hydrolysis switching off downstream signaling because of the extended cell exposure to epinephrine.[23] CAPs are not only involved in adenylate cyclase (AC) association, but in actin binding, SH3 binding, and cell morphology maintenance as well.[24, 25] Previous observations of increased normal RBC membrane filterability after epinephrine treatment for 20 min,[26] explain the enhanced phosphorylated CAP1 in normal RBCs after 30 min epinephrine exposure. Furthermore, Shain et al.[27] suggested that maintenance of altered cell morphology required persistent increased cAMP levels due to continuous PAR stimulation. In contrast, our data suggest that when an increase in ERK activation occurs within 1 min of cell exposure to epinephrine, persistent $\beta_2$AR stimulation has a negative effect on ERK activation and consequently the RBC adhesive function. Based on this analysis, it is expected that inhibition of b-Raf or c-Raf will result in similar effects in SS RBCs as these are additional upstream activators in this pathway.

The inventors believe that key components associated with the ERK pathway could prove to be potential therapeutic targets to alleviate symptoms associated with a hemoglobinopathy such as sickle cell disease. The inventors now demonstrate that G protein-coupled receptor kinase 2 (GRK2) and β-arrestin1/2 could be triggered by activation of the mitogen activated protein kinase ERK pathway. Thus inhibitors of these proteins may result in alleviation of symptoms associated with a hemoglobinopathy such as sickle cell disease. Increased membrane translocation of GRK2 and β-arrestin1/2 and GRK2 and β-arrestin1 activation in SS RBCs may therefore be associated with the pathophysiology of sickle cell disease, making this pathway a therapeutic target for preventing and treating vaso-occlusion, and reversing established vaso-occlusion. The present invention provides methods of alleviating the symptoms of hemoglobinopathies, such as sickle cell disease and β-thalassemia, comprising administering GRK2 and β-arrestin1/2 inhibitors. SS RBCs are characterized by a panoply of abnormalities, including polymerization of deoxygenated HbS, persistent oxidative membrane damage associated with HbS cyclic polymerization, abnormal activation of membrane cation transports, cell dehydration, and cytoskeletal dysfunction. Thus, GRK2 and/or β-arrestin1/2 inhibition may result not only in amelioration of vaso-occlusion, but also other symptoms of sickle cell disease.

Definitions

The subject matter disclosed herein is described using several definitions, as set forth below and throughout the application.

Unless otherwise noted, the terms used herein are to be understood according to conventional usage by those of ordinary skill in the relevant art. In addition to the definitions of terms provided below, it is to be understood that as used in the specification, embodiments, and in the claims, "a", "an", and "the" can mean one or more, depending upon the context in which it is used.

As used herein, "about," "approximately," "substantially," and "significantly" will be understood by persons of ordinary skill in the art and will vary to some extent on the context in which they are used. If there are uses of the term which are not clear to persons of ordinary skill in the art given the context in which it is used, "about" or "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising."

As used herein, the terms "patient" and "subject" may be used interchangeably and refer to one who receives medical care, attention or treatment. As used herein, the term is meant to encompass a person diagnosed with a disease such as a hemoglobinopathy or at risk for developing a hemoglobinopathy (e.g., a person who may be genetically homozygous or heterozygous for a sickle cell-causing mutation, but is not symptomatic). A "patient in need thereof" may include a patient having, suspected of having, or at risk for developing a hemoglobinopathy or symptoms thereof. The subjects may be humans.

As used herein, the term "treatment," "treating," or "treat" refers to care by procedures or application that are intended to alleviate symptoms of a disease (including reducing the occurrence of symptoms of the disease). Although it is preferred that treating a condition or disease such as a hemoglobinopathy will result in an improvement of the condition, the term treating as used herein does not indicate, imply, or require that the procedures or applications are at all successful in alleviating symptoms associated with any particular condition. Treating a patient may result in adverse side effects or even a worsening of the condition which the treatment was intended to improve. Treating may include treating a patient having, suspected of having, or at risk for developing a hemoglobinopathy or symptoms thereof.

Cells may be contacted with the agent directly or indirectly in vivo, in vitro, or ex vivo. Contacting encompasses administration to a cell, tissue, mammal, patient, or human. Further, contacting a cell includes adding an agent to a cell culture. Other suitable methods may include introducing or administering an agent to a cell, tissue, mammal, or patient using appropriate procedures and routes of administration as defined above.

As used herein the term "effective amount" refers to the amount or dose of the agent, upon single or multiple dose administration to the subject, given acutely or chronically, which provides the desired effect in the subject under diagnosis or treatment. The disclosed methods may include administering an effective amount of the disclosed agents (e.g., as present in a pharmaceutical composition) for treating a hemoglobinopathy in the patient, whereby the effective amount alleviates symptoms of the hemoglobinopathy (including reducing the occurrence of symptoms of the hemoglobinopathy).

An effective amount can be readily determined by the attending diagnostician, as one skilled in the art, by the use of known techniques and by observing results obtained under analogous circumstances. In determining the effective amount or dose of agent administered, a number of factors can be considered by the attending diagnostician, such as: the species of the patient; its size, age, and general health; the particular symptoms or the severity of the hemoglobinopathy; the response of the individual patient; the particular agent administered; the mode of administration; the bioavailability characteristics of the preparation administered;

the dose regimen selected; the use of concomitant medication; the length of use of the concomitant medication and other relevant circumstances.

The phrase "alleviates at least one symptom," as used herein, means that a particular treatment results in a lessening of at least one symptom of a disease. Such lessening of a symptom may be a qualitative or quantitative reduction in the severity of the symptom, or may be a reduction in the number of occurrences of the symptom; even though each occurrence may be as severe as it was before the treatment (one or more occurrences may also be less severe). Non-limiting exemplary symptoms of sickle cells disease include vaso-occlusion, acute and chronic painful episodes, chronic hemolysis (aplastic crises), avascular necrosis, infection, end-organ damage, acute chest syndrome, leg ulceration, priapism, and decreased life expectancy. Non-limiting exemplary symptoms of thalassemia include hemolysis, erythroid hyperplasia, biliary tract disease, infection, leg ulcers, extramedullary hematopoiesis, increased risk for developing thromboembolic phenomena, liver and heart damage, and decreased life expectancy.

The term "hemoglobinopathy," as used herein, refers to a condition that is caused by a genetic mutation in a globin gene that results in a mutated hemoglobin α chain or β chain protein, or a condition that is caused by a genetic mutation that results in an abnormal ratio of hemoglobin α chain to β chain or crossover fusion products of 2 globin genes. Non-limiting exemplary hemoglobinopathies include sickle cell disease (including, but not limited to, homozygous for hemoglobin S and a variety of sickle cell syndromes that result from inheritance of the sickle cell gene in compound heterozygosity with other mutant beta globin genes, including, but not limited to, hemoglobin SC disease (HbSC), sickle beta(+) thalassemia, sickle beta(0) thalassemia, sickle alpha thalassemia, sickle delta beta(0) thalassemia, sickle Hb Lepore, sickle HbD, sickle HbO Arab, and sickle HbE), β-thalassemia (including, but not limited to, β-thalassemia major (also known as Cooley's anemia) and β-thalassemia intermedia, and hemoglobin H disease (α-thalassemia with $\alpha^+$-$\alpha^0$ phenotype)). Non-limiting exemplary genetic mutations that cause sickle cell disease include Hb SS, which is hemoglobin with an E6V mutation in each of the two hemoglobin β chains; Hb SC, which is hemoglobin with one β chain with an E6V mutation and one β chain with an E6K mutation; Hb SD, which is hemoglobin with one β chain with an E6V mutation and one β chain with a β121 Glu→Gln mutation; sickle-HbO Arab, which is hemoglobin with one β chain with an E6V mutation and one β chain with a β121(GH4)gGlu→Lys mutation; and Hb SE, which is hemoglobin with one β chain with an E6V mutation and one β chain with an E26K mutation. Non-limiting exemplary genetic mutations that cause β-thalassemia include various 3-mutations, such as IVS II-I, CD 36/37, CD41/42, CD 39; IVS1-6; IVS1-110, CD71/72, IVS1-5, IVS1-1, CD26, IVS2-654, CAP+1, CD19, -28, -29, IVS1-2, InCD (T-G) and CD17; and rare β-mutations, i.e. InCD (A-C), CD8/9, CD43, -86, CD15, Poly A, Poly T/C, IVS2-1, CD1, CD35/36, CD27/28, CD16, CD37, and 619bpDEL. Non-limiting exemplary genetic mutations that cause Hb H disease include $\alpha^+$-$\alpha^0$ phenotypes such as α2 Poly A (AATAAA→AATA-), α2 Poly A (AATAAA→AATGAA), and α2 Poly A (AATAAA→AATAAG); $\alpha^+$ phenotypes such as α2 CD 142 (TAA→CAA), α2 CD 142 (TAA→AAA), and α2 CD 142 (TAA→TAT); and $\alpha^0$ phenotypes such as $-\alpha^{3.7}$ Init CD (ATG→GTG), $-^{SEA}$, $-^{THAI}$, $-^{MED\ II}$, $-^{BRIT}$, $-^{MED\ I}$, $-^{SA}$, $-(\alpha)^{20.5}$, and $-^{FIL}$.

The term "β-arrestin1/2 inhibitor," as used herein, refers to an inhibitor of β-arrestin1/2 kinase membrane translocation and activity. A β-arrestin1/2 inhibitor may be any type of molecule, including, but not limited to, small molecules, inhibitory antibodies and expression modulators (such as antisense molecules, microRNAs, siRNAs, aptamers, etc.), and may act directly on the β-arrestin1/2 protein, may interfere with expression of the β-arrestin1/2 protein (e.g., transcription, splicing, translation, and/or post-translational processing), and/or may prevent improper intracellular localization and/or membrane translocation of the β-arrestin1/2 protein.

The term "GRK2 inhibitor," as used herein, refers to an inhibitor of GRK2 kinase membrane translocation and activity. A GRK2 inhibitor may be any type of molecule, including, but not limited to, small molecules, antibodies and expression modulators (such as antisense molecules, microRNAs, siRNAs, aptamers, etc.), and may act directly on the GRK2 protein, may interfere with expression of the GRK2 protein (e.g., transcription, splicing, translation, and/or post-translational processing), and/or may prevent improper intracellular localization and/or membrane translocation and phosphorylation of the GRK2 protein. A GRK2 inhibitor includes βARK1.

In some embodiments, methods of alleviating at least one symptom of a hemoglobinopathy in a subject are provided. Such methods comprise, in some embodiments, administering to the patient an inhibitor selected from a β-arrestin1/2 inhibitor and a GRK2 inhibitor. Non-limiting exemplary hemoglobinopathies include β-thalassemia, sickle cell disease and Hemoglobin H.

For the treatment of sickle cell disease or other hemoglobinopathies, in some embodiments, at least one symptom that may be alleviated by administering the inhibitors described herein is selected from vaso-occlusion, acute or chronic painful episodes, chronic hemolysis (aplastic crises), avascular necrosis, infection, end-organ damage, and erythroid hyperplasia. In some embodiments, alleviating a symptom of sickle cell disease means reducing the amount, frequency, duration or severity of the symptom. For example, for vaso-occlusion, in some embodiments, alleviating the symptom includes preventing, reducing and/or reversing the average size of the vaso-occlusions, and/or reducing the number and/or frequency of vaso-occlusions. Further, alleviating a symptom may or may not result in a reduction in the discomfort experienced by the patient as a result of the symptom. That is, in some embodiments, while the number and/or average size of vaso-occlusions may be reduced following a treatment described herein, the patient may or may not experience a similar reduction in acute or chronic pain caused by vaso-occlusion.

In some embodiments, when vaso-occlusion is alleviated by administration of an inhibitor described herein, acute painful episodes are also alleviated (i.e., the number and/or severity is reduced). In some embodiments, when vaso-occlusion is alleviated by administration of an inhibitor described herein, hemolysis is also alleviated. In some embodiments, vascular endothelial injury is alleviated by administration of an inhibitor described herein. In some embodiments, when hemolysis is alleviated by administration of an inhibitor described herein, the incidence of infections is reduced. In some embodiments, when hemolysis is alleviated by administration of an inhibitor described herein, erythroid hyperplasia is also alleviated. In some embodiments, when vaso-occlusion and/or hemolysis are alleviated by administration of an inhibitor described herein, end-organ damage is also alleviated.

In some embodiments, methods of inhibiting and/or reversing adhesion of sickle red blood cells to endothelial cells are provided. In some embodiments, methods of inhibiting and/or reversing adhesion of sickle red blood cells to leukocytes are provided. In some embodiments, methods of inhibiting and/or reversing activation of leukocytes and leukocyte adhesion by sickle red blood cells are provided. Such methods comprise, in some embodiments, contacting the sickle red blood cells with an inhibitor selected from a β-arrestin1/2 inhibitor and a GRK2 inhibitor.

In some embodiments, methods of inhibiting adhesion of sickle red blood cells to endothelial cells in a patient are provided. In some embodiments, methods of inhibiting adhesion of sickle red blood cells to leukocytes and sickle red blood cell-induced leukocyte activation and adhesion to endothelial cells in a patient are provided. Such methods comprise, in some embodiments, administering to the patient an inhibitor selected from a β-arrestin1/2 inhibitor and a GRK2 inhibitor.

In some embodiments, a method comprises administering to the patient or subject, or contacting a sickle red blood cell with, a β-arrestin1/2 inhibitor and/or a GRK2 inhibitor. In some embodiments, a method comprises administering to the patient or subject, or contacting a sickle red blood cell with, a β-arrestin1/2 inhibitor. Non-limiting exemplary β-arrestin1/2 inhibitors include anti-sense RNAs, siRNAs, antibodies and small molecule inhibitors of β-arrestin1/2. In some embodiments, a method comprises administering to the patient or subject, or contacting a sickle red blood cell with, a GRK2 inhibitor. A non-limiting exemplary GRK2 inhibitor is βARK1. Non-limiting exemplary GRK2 inhibitors include anti-sense RNAs, siRNAs, antibodies and small molecule inhibitors of GRK2.

In some embodiments, a method of inhibiting formation of multicellular aggregates in the presence of sickle red blood cells or in a subject with sickle cell disease is provided. The method comprises administering to the patient or subject with sickle cell disease, or contacting a sickle red blood cell with an inhibitor selected from a β-arrestin1/2 inhibitor and a GRK2 inhibitor.

In some embodiments, a method of inhibiting activation and adhesion of leukocytes to endothelial cells in the presence of sickle red blood cells or in a subject with sickle cell disease is provided. The method comprises administering to the patient or subject with sickle cell disease, or contacting the sickle red blood cells with an inhibitor selected from a β-arrestin1/2 inhibitor and a GRK2 inhibitor.

In some embodiments, a method of alleviating at least one of acute or chronic pain, chronic hemolysis (aplastic crises), avascular necrosis, organ damage, and erythroid hyperplasia in subjects with sickle cell disease is provided. The method comprises administering to the patient or subject with sickle cell disease, or contacting the sickle red blood cells with an inhibitor selected from a β-arrestin1/2 inhibitor and a GRK2 inhibitor.

In some embodiments, a method comprises administering to the patient, or contacting a sickle red blood cell with a combination of two or more inhibitors selected from a β-arrestin1/2 inhibitor and a GRK2 inhibitor. The two or more inhibitors may be co-administered. Co-administration indicates the inhibitors may be administered in any order, at the same time or as part of a unitary composition. The two inhibitors may be administered such that one inhibitor is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks or more.

Administration to a subject may include formulating the therapeutic agents, such as a β-arrestin1/2 inhibitor and/or a GRK2 inhibitor, with pharmaceutically acceptable carriers and/or excipients, etc., to form pharmaceutical compositions. Suitable formulations for therapeutic compounds are available to those skilled in the art. Administration may be carried out by any suitable method, including intraperitoneal, intravenous, intramuscular, intrathecal, subcutaneous, transcutaneous, oral, nasopharyngeal, or transmucosal absorption among others. The dosage for a particular subject may be determined based on, for example, the subject's weight, height, and/or age; the severity of the subject's disease or symptoms; the length of treatment and/or number of doses anticipated in a particular regiment; the route of administration; etc.

Our data also indicated that the intensity of basal ERK phosphorylation and the levels of GRK2 and β-arrestin1/2 bound to the membrane vary among patients with sickle cell disease. Thus, β-arrestin1/2 and GRK2 translocation to the membrane as well as ERK phosphorylation can be used as a prognostic tool for sickle cell severity. For this end, we plan to screen patients both when they are asymptomatic during steady state and during vaso-occlusive crisis for RBC ERK phosphorylation, and GRK2 and β-arrestin1/2 membrane recruitment and phosphorylation prior to and optionally after treatment with at least one of Cholera toxin, Pertussis toxin and epinephrine, and determine the relation between kinase (ERK, GRK2 and β-arrestin1/2) activation and/or expression levels and adhesion of these sickle red blood cells to endothelial cells. This will help determine sickle cell severity, and could also help predict precipitation of painful vaso-occlusive crisis.

The following examples are illustrative and are not intended to limit the disclosed subject matter. All references cited herein are incorporated herein by reference in their entireties.

EXAMPLES

Example 1: Materials and Methods

Endothelial Cells.

Primary human umbilical vein endothelial cells (HUVECs) were grown as monolayers in EBM2 medium (Lonza Walkersville, Inc., Walkersville, Md.) supplemented with EGM2 (Lonza Walkersville) as described previously.[4] EC passage was accomplished with trypsinization, as required. Cells were used until they reached the 5th passage. For flow chamber experiments, HUVECs were cultured until they reached confluence on clear glass slides precoated with 2% gelatin.

Antibodies.

Antibodies used included the following monoclonal and polyclonal antibodies (Abs, as purified immunoglobulin [Ig] unless otherwise noted): BS46 (mouse anti-ICAM-4, generously provided by Dr. Jean-Pierre Cartron, INSERM Unité 665, Paris, France);[28] and mouse anti-phospho-myelin basic protein (Millipore, Temecula, Calif.); mouse anti-human transferrin receptor (BD Biosciences, San Jose, Calif.); and mouse anti-human glycophorin C and A produced in our laboratory. Rabbit anti-human ERK1/2 was from Upstate, Charlottesville, Va.; rabbit anti-human phospho-ERK1/2 was from Cell Signaling Technology, Danvers, Mass. Rabbit anti-human MAPK kinase (MEK1/2); anti-human GRK2; anti-human phospho-GRK2; and anti-human β arrestin1 were from Sigma-Aldrich, St. Louis, Mo. Rabbit anti-human β arrestin1/2 was generously provided by Dr. Robert J.

Lefkowitz at Duke University. The murine myeloma protein P3x63/Ag8 (P3 ascitc fluid, diluted 1:500) was used as a non-reactive control murine Ig for mAbs.[29] In all studies, Abs were used at saturating dilutions unless otherwise indicated.

Collection, Preparation and Treatment of RBCs.

Sickle cell patient donors had not been transfused for at least three months, had not experienced vaso-occlusion for three weeks. Fresh blood samples from patients homozygous for hemoglobin S and from healthy donors were collected into citrate tubes. Blood was used within less than 24 h of collection. Packed RBCs were separated as previously described in detail.[5] RBCs were separated from the buffy coat containing leukocytes and platelet-rich plasma by gravity at 4° C. for at least 2 h. Plasma and buffy coat were removed by aspiration, and RBCs were washed four or five times in sterile PBS with 1.26 mM $Ca^{2+}$, 0.9 mM $Mg^{2+}$ (pH 7.4). Packed RBCs were analyzed for leukocyte and platelet contamination using an Automated Hematology Analyzer Sysmex K-1000 (Sysmex, Co., Cobe, Japan).

Aliquots of packed RBCs were treated with various reagents to affect cAMP signaling or protein phosphorylation. Sham-treated RBCs were incubated with the same buffer and vehicle, but without the active agent. Unless otherwise indicated, RBCs were treated at 37° C. with one or more of the following reagents: 20 nM epinephrine (Sigma-Aldrich, St. Louis, Mo.) for 1 min; 2 μg/ml Pertussis toxin (PTx, Calbiochem, La Jolla, Calif.) for 30 min; 2 μg/ml Cholera toxin (CT, Calbiochem) for 10 min; 10 μM MEK1/2 inhibitor (MEKI, U0126, Calbiochem) or 10 μM BARK1 inhibitor (Calbiochem) for 1 h. Treated RBCs were then washed 5 times with 4 ml PBS with $Ca^{2+}$ and $Mg^{2+}$. Normal RBCs were used as controls. Prior to adhesion assays, treated RBCs were labeled with PKH 26 red fluorescent cell linker kit (Sigma), following the manufacturer's instructions.

For in vitro adhesion assays, human SS RBCs were sham-treated with buffer and vehicle alone or treated at 37° C. with the GRK2 inhibitor, BARK1 at 10 μM for 1 h, followed or not by treatment with 2 μg/ml Cholera toxin for 10 min. Cells were then washed three times with 5 ml PBS with $Ca^{2+}$ and $Mg^{2+}$. Prior to adhesion assays, washed treated SS RBCs were labeled with PKH 26 red fluorescent cell linker kit (Sigma-Aldrich, St. Louis, Mo.), following the manufacturer's instructions.

For some in vivo adhesion studies, packed SS RBCs were fluorescently labeled with the dye DiI (Molecular Probes Inc., Eugene, Oreg.), following the manufacturer's instructions, prior to cell treatment. DiI has been used in previous in vivo studies, and this dye has no effect on RBC suspension viscosity and RBC survival in circulation.[30] Cell morphology was checked by microscopy.

Western Blot.

Treated packed RBCs were lysed with hypotonic buffer (5 mM $Na_2HPO_4$+1 mM EDTA+0.1% $NaN_3$, pH 8) containing 2 mM phenylmethylsulphonylfluoride (PMSF, Sigma), phosphatase inhibitor cocktail (Sigma) and protease inhibitor cocktail (Sigma). Protein separation by polyacrylamide gel electrophoresis using equal amounts of total RBC membrane ghost proteins per lane, after correcting total protein measurements for residual hemoglobin content, and Western blot[31] using the appropriate Ab were then performed. Glycohporin C and A were used as a loading control. Bands were analyzed densitometrically using ImageJ software downloaded from the NIH website. PhosphoERK data were normalized according to total ERK, and is presented as fold change in ERK phosphorylation.

Flow Chamber Assays.

Graduated height flow chambers were used to quantify adhesion of RBCs to HUVECs substantially as previously described in detail.[4, 32] Slides coated with HUVECs were then washed three times with 20 ml HBSS with 1.26 mM $Ca^{2+}$, 0.9 mM $Mg^{2+}$ (Gibco, Grand Island, N.Y.) warmed previously to 37° C. and then fit into a variable height flow chamber. The flow chamber was mounted on the stage of an inverted phase contrast microscope (Diaphot, Nikon Inc., Melville, N.Y.) connected to a thermoplate (Tokai Hit Co., Ltd., Japan) set at 37° C. Cells were observed using a video camera (RS photometrics,) attached to the microscope and connected to a Macintosh G4 computer. RBC (3 ml) suspended at 0.2% (vol/vol) in HBSS with $Ca^{2+}$, $Mg^{2+}$ were infused into the flow chamber and allowed to adhere to the slide for 10 min without flow. Before exposure to flow, a minimum of three fields at each of seven different locations along a line oriented normal to future flow were examined for the total number of fluorescent cells. Fluid flow (HBSS with $Ca^{2+}$, $Mg^{2+}$) was then started using a calibrated syringe pump. After exposure to flow, the fields were again examined and the number of adherent cells counted. The fraction of adherent cells was presented as (number of cells attached after exposure to flow)/(cells present per field before flow). The wall shear stress was calculated as:

$$\tau_w = \frac{6\mu Q}{wH(x)^2}$$

$\tau_w$=wall shear stress (dyne/$cm^2$); Q=volumetric flow rate ($cm^3$/s); μ is media viscosity, w is the width of the flow channel, and H(x) is the height of the flow chamber as a function of position along the microscope slide. Several investigators have shown that blood flow in small vessels may be continuous, with shear stresses of 1-2 dynes/$cm^2$, or flow may be intermittent. Our data were obtained using both intermittent and continuous flow conditions.

Mice:

All animal experiments were carried out in accordance with protocols approved by the Duke University Animal Care and Use Committee. Female athymic homozygous nude mice (nu-/nu-) were between 8-12 weeks of age (Charles River Laboratories, Wilmington, Mass.).

Window Chamber Surgery:

General anesthesia was achieved by intra-peritoneal injection of 100 mg/kg of ketamine (Abbott Laboratory, Chicago, Ill.) and 10 mg/kg of xylazine (Bayer, Shawnee Mission, Kans.). A double-sided titanium frame window chamber was surgically implanted into the dorsal skin fold under sterile conditions using a laminar flow hood. Surgery involved carefully removing the epidermal and dermal layers of one side of a dorsal skin fold, exposing the blood vessels of the subcutaneous tissue adjacent to the striated muscles of the opposing skin fold, and then securing the two sides of the chamber to the skin using stainless steel screws and sutures. A glass window was placed in the chamber to cover the exposed tissue and secured with a snap ring. Subsequently, animals were kept at 32-34° C. until in vivo studies were performed 3 days post-surgery.

RBC Infusions and Intravital Microscopy:

Animals were infused with washed SS RBCs (300 μl hematocrit (Hct) 50% in saline) treated with epinephrine at 20 nM for 1 min or 5 μM βARK1 for 1 hour followed by treatment with 20 nM epinephrine for 1 min. Animals were then placed on the stage of an Axoplan microscope (Carl Zeiss, Thornwood, N.Y.); temperature was maintained at 37° C. using a thermostatically controlled heating pad. RBC adhesion and blood flow dynamics were observed in subdermal vessels for at least 30 minutes using 20× and 10× magnifications. Microcirculatory events and cell adhesion were simultaneously recorded using a Trinitron Color video monitor (PVM-1353 MD, Sony) and JVC videocassette recorder (BR-S3784, VCR King, Durham, N.C.) connected to a digital video camera C2400 (Hamamatsu Photonics K.K., Japan). Arterioles were distinguished from venules based on: 1) observation of divergent flow as opposed to convergent flow; 2) birefringent appearance of vessel walls using transillumination, which is characteristic of arteriolar vascular smooth muscle; and 3) relatively straight vessel trajectory without evidence of tortuosity. Cells were considered adherent when they attach to the vessel walls and become immobile for 1 minute.

Statistical Analysis.

Data were compared using parametric analyses (GraphPad Prism 4 Software, San Diego, Calif.), including repeated and non-repeated measures of analysis of variance (ANOVA). One-way ANOVA analyses were followed by Bonferroni corrections for multiple comparisons (multiplying the p value by the number of comparisons). A p value <0.05 was considered significant.

Example 2: The Role of Sickle Cell ERK Signaling in GRK2 and β-Arrestin-1/2

Translocation of β-arrestin1/2 and GRK2 to the membrane, and phosphorylation of GRK2, β-arrestin-1 and the mitogen activated protein kinase ERK in sickle red cells (SSRBCs) appear to be dependent on $G\alpha_s$ protein activation. We have data suggesting that activation of ERK signaling triggers GRK2 membrane-translocation and its phosphorylation, which in turn increase membrane-recruitment of β-arrestin1/2 and phosphorylation. We will determine if this pathway activates RBC adhesion molecules involved in both adhesion to ECs and activation of leukocytes. To accomplish these studies, we will use inhibitors of GRK2 and β-arrestin-1/2-receptor coupling to inhibit kinase membrane-translocation.

Regulation of GRK2 by ERK modules can be relevant in pathological situations where GRK2 levels are altered and can be deleterious[33, 34], and GRK2 inhibition can be a viable therapeutic approach[33]. The contribution of RBC ERK activation in GRK2 and β-arrestin1/2 signaling, and in RBC adhesion receptor activation remain unknown and need to be addressed. The abnormal RBC is central to the vaso-occlusive pathology of SCD, and GRK2 and β-arrestin1/2 functional sequelae represent a novel area of study.

Figure 1A:
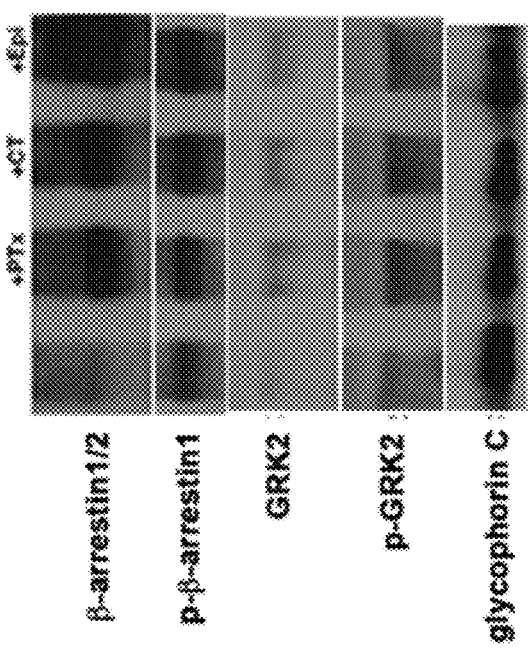
FIG. 1. Membrane-translocation and phosphorylation of β-arrestin1/2 and GRK2 are dependent on activation of $G\alpha_s$ protein. SSRBCs (n=3) were sham-treated, or treated with 2 µg/ml Pertussis toxin (PTx), which suppresses activation of Gi protein, for 30 min; 2 µg/ml Cholera toxin (CT), which directly activates Gs protein, for 10 min; or 20 nM epinephrine (Epi) for 1 min. Forty µg of membrane protein ghosts were used per lane. A. Protein membrane ghosts were blotted for the total amounts of β-arrestin1/2 and GRK2, and for phosphorylated β-arrestin1 and phosphorylated GRK2. An anti-glycophorin C antibody is used as a loading control.
Figure 1B:
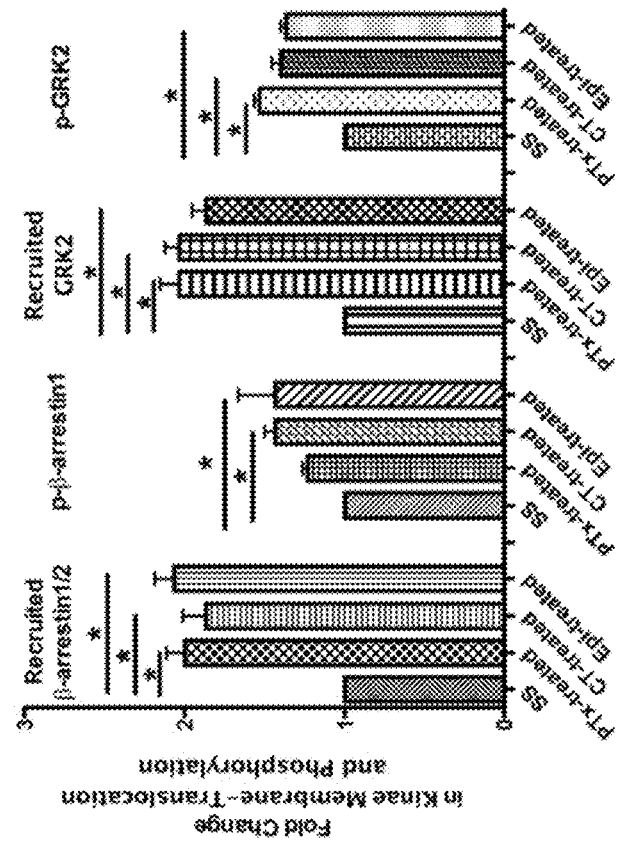
Figure 3B:
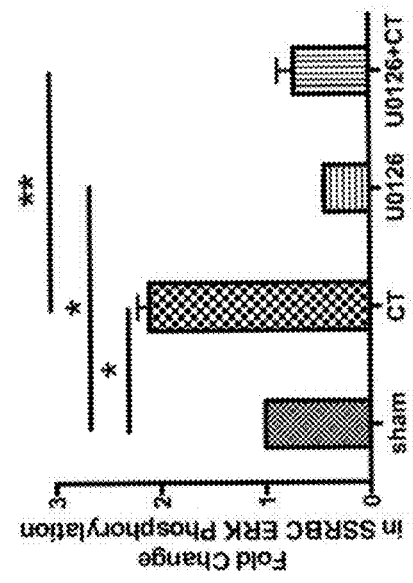

Our preliminary studies show that SS RBC membrane translocation of β-arrestin1/2 and GRK2, and phosphorylation of both GRK2 and β-arrestin1, significantly increased as a result of activation of $G\alpha_s$ (FIG. 1, n=3). Treatment of SS RBCs with Pertussis toxin (PTx), which inhibits activation of $G\alpha_i$ protein-mediating suppression of $G\alpha_s$, significantly increased both membrane-recruitment of β-arrestin-1/2 (FIGS. 1A&B) and GRK2 (FIGS. 1A&B), and phosphorylation of GRK2 (FIGS. 1A&B). Similarly, Cholera toxin (CT), which activates $G\alpha_s$, and epinephrine (Epi), which stimulates β2-ARs, also enhanced β-arrestin1/2 and GRK2 membrane translocation, and phosphorylation of both GRK2 and β-arrestin1 (FIGS. 1A&B). However, β-arrestin1 phosphorylation did not show significant increase by PTx treatment (FIGS. 1A&B). These data suggest that both increased recruitment of β-arrestin1/2 and GRK2, and phosphorylation of GRK2 and β-arrestin1 are dependent on $G\alpha_s$. Contrary to SS RBCs, PTx, CT and Epi treatment of AA RBCs failed to increase membrane-recruitment of β-arrestin1/2 and GRK2, and basal phosphorylation of GRK2 and β-arrestin1 (FIG. 2, n=4, p>0.05). ERK phosphorylation was also enhanced upon SS RBC treatment with CT (FIGS. 3A&B, n=3), PTx (previously published data)[35] and Epi (previously published data)[35]; an effect inhibited with U0126 MEK inhibitor, suggesting that ERK activation is also $G\alpha_s$-dependent. Additionally, the amounts of membrane-bound β-arrestin1/2 in AA RBCs (n=2) were significantly higher than in SS RBCs (n=3) (FIGS. 4A&B). However, the levels of membrane-bound β-arrestin1/2 in SSRBCs increased with PTx treatment (FIGS. 4A&B). Thus, our data underscore the significance of RBC β-arrestin1/2 and GRK2 membrane translocation under pathophysiological conditions, and suggest that ERK activation may trigger GRK2 and β-arrestin1/2, and can be dependent on $G\alpha_s$.

Example 3: GRK2 is Involved in Interactions of SSRBCs with the Endothelium and Leukocytes We have previously shown that MEK-dependent ERK signaling in non-stimulated SS RBCs is required for RBC adhesive interaction with both normal (non-activated) and TNFα activated endothelial cells, and that RBC ERK signaling regulates activation of leukocyte adhesion. Co-incubation of SS RBCs with naive polymorphonuclear cells (PMNs), resulted in increased PMN adhesion to ECs. However, inhibition of ERK with the MEK inhibitors U0126, RDEA119, GSK1120212 and AZD6244 decreased the ability of SS RBCs to promote PMN adhesion, suggesting that ERK signaling activation regulates activation of RBC adhesion receptors.

Cholera toxin treatment of SS RBCs increased adhesion of these sickle red cells to endothelial cells, an effect inhibited by the GRK2 inhibitor βARK1 (FIG. 5). These data demonstrate that GRK2 signaling is involved in SS RBC adhesion to endothelial cells, and suggest that SS RBC adhesive interactions with the endothelium is regulated by increased GRK2 recruitment to the membrane and its phosphorylation. We also expected that GRK2 inhibitor βARK1 could inhibit the ability of SSRBCs to activate leukocyte adhesion, since the ERK pathway activation likely triggers GRK2 activation.

Example 4: Sickle Cell ERK Signaling Promotes GRK2 Membrane Recruitment and Activation Our new data confirm that SSRBC membrane translocation of GRK2 and its phosphorylation significantly increased as a result of activation of $G\alpha_s$ (FIG. 6, n=5). Treatment of SS RBCs with PTx increased both membrane-recruitment of GRK2 and its phosphorylation (FIGS. 6A&C). Similarly, CT also induced enhanced GRK2 membrane translocation and phosphorylation (FIG. 6A-D). However, the effects induced by CT and PTx were inhibited with the GRK2 inhibitor βARK1, indicating that GRK2 acts downstream of $G\alpha_s$ protein (FIG. 6A-D). U0126, a MEK inhibitor, also had an inhibitory effect on CT- and PTx-induced GRK2 membrane translocation and phosphorylation, suggesting that ERK is an upstream effector of GRK2 activation. Thus, our data highlights one of the molecular mechanisms by which RBC GRK2 contributes to the pathophysiological conditions, and suggests that ERK activation triggers GRK2 activation, both of which can be dependent on $G\alpha_s$.

Example 5: Sickle Cell ERK Signaling and GRK2 Membrane Recruitment and Activation Initiate β-Arrestin-1/2 Signaling To determine that β-arrestin1/2 acts downstream of ERK and GRK2, SS RBCs were treated with the MEK inhibitor U00126 to prevent ERK activation or the GRK2 inhibitor βARK1, followed by PTx or CT stimulation. Our new data show once more that SS RBC membrane translocation of β-arrestin1/2 and phosphorylation β-arrestin1 significantly increased as a result of activation of Go, with CT or PTx treatment (FIG. 7, n=5). However, treatment with the GRK2 inhibitor βARK1 and U0126 MEK inhibitor significantly decreased β-arrestin1/2 membrane translocation and β-arrestin1 phosphorylation induced by CT treatment of SS RBCs (FIG. 7A-D). Similarly, the GRK2 inhibitor βARK1 also inhibited the effect of PTx on β-arrestin1/2 recruitment to the membrane (FIGS. 7A&C). In contrast, U0126 MEK inhibitor failed to have an effect on PTx treatment and decrease β-arrestin1/2 binding to the membrane (FIGS. 7A&C). Together, our data suggest that activation of $G\alpha_s$ protein leads to increased activation of ERK1/2. As a result, GRK2 is recruited to the membrane and phosphorylated, which in turn attracts β-arrestin1/2 translocation to the membrane and activation.

Example 6: GRK2 Contributes to SS RBC Adhesion to Vascular Endothelium and Vaso-Occlusion In Vivo The following experiment was designed to determine whether GRK2 can be targeted therapeutically to prevent SS RBC adhesion to the vascular endothelium and vaso-occlusion in vivo.

To further these studies, we tested whether inhibition of GRK2 with the GRK2 inhibitor βARK1 prevents human SS RBC-induced vaso-occlusion. Human SS RBCs were treated with the GRK2 inhibitor βARK1 followed by epinephrine treatment ex vivo, then extensively washed prior to administration to nude mice. Intravital microscopy studies showed that infusion of epinephrine-treated human SS RBCs to nude mice (n=2), showed marked adhesion in inflamed venules and induced occlusion of small diameter (9-25 μm) vessels. SS RBC adhesion was also observed in much larger vessels than 25 μm in diameter, indicating that human SS RBC-induced vaso-occlusion was not a result of trapping of human SS RBCs in vessels with diameters ≤8 μm, since the size of human RBC is 8 μm in diameter (FIG. 8A). However, inhibition of the effect of epinephrine on GRK2 in human SS RBCs with the GRK2 inhibitor βARK1 ex-vivo prior to RBC infusion to animals (n=2), dramatically decreased both human SS RBC adhesion and vessel obstruction (FIG. 8B). These data suggest that inhibition with the GRK2 inhibitor βARK1 of GRK2 translocation to the membrane and activation improved SS RBC circulatory behavior due to amelioration of SS RBC adhesive function. Thus, our data suggest that GRK2 and its mechanism of action could represent a novel target for the treatment of SCD pathophysiology.

REFERENCES

1. Frenette P S, Atweh G F: Sickle cell disease: old discoveries, new concepts, and future promise, J Clin Invest 2007, 117:850-858
2. Hebbel R P, Boogaerts M A, Eaton J W, Steinberg M H: Erythrocyte adherence to endothelium in sickle-cell anemia. A possible determinant of disease severity, N Engl J Med 1980, 302:992-995
3. Mohandas N, Evans E: Sickle erythrocyte adherence to vascular endothelium. Morphologic correlates and the requirement for divalent cations and collagen-binding plasma proteins, J Clin Invest 1985, 76:1605-1612
4. Zennadi R, Hines P C, De Castro L M, Cartron J P, Parise L V, Telen M J: Epinephrine acts through erythroid signaling pathways to activate sickle cell adhesion to endothelium via LW-alphavbeta3 interactions, Blood 2004, 104:3774-3781
5. Zennadi R, Chien A, Xu K, Batchvarova M, Telen M J: Sickle red cells induce adhesion of lymphocytes and monocytes to endothelium, Blood 2008, 112:3474-3483
6. Zennadi R, Moeller B J, Whalen E U, Batchvarova M, Xu K, Shan S, Delahunty M, Dewhirst M W, Telen M J: Epinephrine-induced activation of LW-mediated sickle cell adhesion and vaso-occlusion in vivo, Blood 2007, 110:2708-2717
7. Schmitt J M, Stork P J: beta 2-adrenergic receptor activates extracellular signal-regulated kinases (ERKs) via the small G protein rap1 and the serine/threonine kinase B-Raf, J Biol Chem 2000, 275:25342-25350
8. Houslay M D, Kolch W: Cell-type specific integration of cross-talk between extracellular signal-regulated kinase and cAMP signaling, Mol Pharmacol 2000, 58:659-668
9. Kolch W: Meaningful relationships: the regulation of the Ras/Raf/MEK/ERK pathway by protein interactions, Biochem J 2000, 351 Pt 2:289-305
10. Brzostowski J A, Kimmel A R: Signaling at zero G: G-protein-independent functions for 7-TM receptors, Trends Biochem Sci 2001, 26:291-297
11. Hall R A, Premont R T, Chow C W, Blitzer J T, Pitcher J A, Claing A, Stoffel R H, Barak L S, Shenolikar S, Weinman E J, Grinstein S, Lefkowitz R J: The beta2-adrenergic receptor interacts with the Na+/H+-exchanger regulatory factor to control Na+/H+ exchange, Nature 1998, 392:626-630
12. Ballas S K, Smith E D: Red blood cell changes during the evolution of the sickle cell painful crisis, Blood 1992, 79:2154-2163
13. Billett H H, Kim K, Fabry M E, Nagel R L: The percentage of dense red cells does not predict incidence of sickle cell painful crisis, Blood 1986, 68:301-303
14. Kaul D K, Chen D, Zhan J: Adhesion of sickle cells to vascular endothelium is critically dependent on changes in density and shape of the cells, Blood 1994, 83:3006-3017
15. Kaul D K, Fabry M E, Nagel R L: Vaso-occlusion by sickle cells: evidence for selective trapping of dense red cells, Blood 1986, 68:1162-1166
16. Lawrence C, Fabry M E, Nagel R L: Red cell distribution width parallels dense red cell disappearance during painful crises in sickle cell anemia, The Journal of laboratory and clinical medicine 1985, 105:706-710
17. Orringer E P, Casella J F, Ataga K I, Koshy M, Adams-Graves P, Luchtman-Jones L, Wun T, Watanabe M, Shafer F, Kutlar A, Abboud M, Steinberg M, Adler B, Swerdlow P, Terregino C, Saccente S, Files B, Ballas S, Brown R, Wojtowicz-Praga S, Grindel J M: Purified poloxamer 188 for treatment of acute vaso-occlusive crisis of sickle cell disease: A randomized controlled trial, JAMA: the journal of the American Medical Association 2001, 286:2099-2106

18. Hines P C, Zen Q, Burney S N, Shea D A, Ataga K I, Orringer E P, Telen M J, Parise L V: Novel epinephrine and cyclic AMP-mediated activation of BCAM/Lu-dependent sickle (SS) RBC adhesion, Blood 2003, 101: 3281-3287
19. Gayen Betal S, Setty B N: Phosphatidylserine-positive erythrocytes bind to immobilized and soluble thrombospondin-1 via its heparin-binding domain, Translational research: the journal of laboratory and clinical medicine 2008, 152:165-177
20. Zennadi R, Whalen E J, Soderblom E J, Alexander S C, Thompson J W, Dubois L G, Moseley M A, Telen M J: Erythrocyte plasma membrane-bound ERK1/2 activation promotes ICAM-4-mediated sickle red cell adhesion to endothelium, Blood 2012, 119:1217-1227
21. Fukumoto T, Kubota Y, Kitanaka A, Yamaoka G, Ohara-Waki F, Imataki O, Ohnishi H, Ishida T, Tanaka T: Gabi transduces PI3K-mediated erythropoietin signals to the Erk pathway and regulates erythropoietin-dependent proliferation and survival of erythroid cells, Cell Signal 2009, 21:1775-1783
22. Jindal H K, Ai Z, Gascard P, Horton C, Cohen C M: Specific loss of protein kinase activities in senescent erythrocytes, Blood 1996, 88:1479-1487
23. Rochais F, Vandecasteele G, Lefebvre F, Lugnier C, Lum H, Mazet J L, Cooper D M, Fischmeister R: Negative feedback exerted by cAMP-dependent protein kinase and cAMP phosphodiesterase on subsarcolemmal cAMP signals in intact cardiac myocytes: an in vivo study using adenovirus-mediated expression of CNG channels, J Biol Chem 2004, 279:52095-52105
24. Hubberstey A V, Mottillo E P: Cyclase-associated proteins: CAPacity for linking signal transduction and actin polymerization, FASEB J 2002, 16:487-499
25. Bertling E, Hotulainen P, Mattila P K, Matilainen T, Salminen M, Lappalainen P: Cyclase-associated protein 1 (CAP1) promotes cofilin-induced actin dynamics in mammalian nonmuscle cells, Mol Biol Cell 2004, 15:2324-2334
26. Tuvia S, Moses A, Gulayev N, Levin S, Korenstein R: Beta-adrenergic agonists regulate cell membrane fluctuations of human erythrocytes, The Journal of physiology 1999, 516 (Pt 3):781-792
27. Shain W, Forman D S, Madelian V, Turner J N: Morphology of astroglial cells is controlled by beta-adrenergic receptors, J Cell Biol 1987, 105:2307-2314
28. Bloy C, Blanchard D, Hermand P, Kordowicz M, Sonneborn H H, Cartron J P: Properties of the blood group LW glycoprotein and preliminary comparison with Rh proteins, Mol Immunol 1989, 26:1013-1019
29. Galfre G, Howe S C, Milstein C, Butcher G W, Howard J C: Antibodies to major histocompatibility antigens produced by hybrid cell lines, Nature 1977, 266:550-552
30. Unthank J L, Lash J M, Nixon I C, Sidner R A, Bohlen H G: Evaluation of carbocyanine-labeled erythrocytes for microvascular measurements, Microvascular research 1993, 45:193-210
31. Towbin H, Staehelin T, Gordon J: Electrophoretic transfer of proteins from polyacrylamide gels to nitrocellulose sheets: procedure and some applications, Proc Natl Acad Sci USA 1979, 76:4350-4354
32. Udani M, Zen Q, Cottman M, Leonard N, Jefferson S, Daymont C, Truskey G, Telen M J: Basal cell adhesion molecule/lutheran protein. The receptor critical for sickle cell adhesion to laminin, J Clin Invest 1998, 101:2550-2558
33. Rengo G, Lymperopoulos A, Leosco D, Koch W J: GRK2 as a novel gene therapy target in heart failure, Journal of molecular and cellular cardiology 2011, 50:785-792
34. Penela P, Murga C, Ribas C, Salcedo A, Jurado-Pueyo M, Rivas V, Aymerich I, Mayor F, Jr.: G protein-coupled receptor kinase 2 (GRK2) in migration and inflammation, Archives of physiology and biochemistry 2008, 114:195-200

I claim:

1. A method of alleviating at least one symptom of sickle cell disease in a subject comprising administering an inhibitor selected from a β-arrestin1/2 inhibitor comprising a small molecule inhibitor that acts directly on the β-arrestin1/2 protein and a GRK2 inhibitor comprising a small molecule inhibitor that acts directly on the GRK protein to the subject, wherein the at least one symptom is selected from vaso-occlusion, acute or chronic painful episodes, chronic hemolysis (aplastic crises), avascular necrosis, infection, end-organ damage, and erythroid hyperplasia.

2. The method of claim 1, wherein the subject is human.

3. The method of claim 1, wherein the inhibitor is a GRK2 inhibitor.

4. The method of claim 3, wherein the GRK2 inhibitor is βARK1.

5. A method of inhibiting adhesion of sickle red blood cells in a subject with sickle cell disease comprising administering an inhibitor selected from a β-arrestin1/2 inhibitor comprising a small molecule inhibitor that acts directly on the β-arrestin1/2 protein and a GRK2 inhibitor comprising a small molecule inhibitor that acts directly on the GRK protein to the subject to inhibit adhesion of the sickle red blood cells.

6. The method of claim 5, wherein the adhesion is between the sickle red blood cells and endothelial cells.

7. The method of claim 5, wherein the adhesion is between the sickle red blood cells and leukocytes.

8. The method of claim 7, wherein administration of the inhibitor blocks activation of the leukocytes in the subject.

9. The method of claim 5, wherein administration of the inhibitor inhibits formation of multicellular aggregates in the presence of sickle red blood cells in the subject.

10. The method of claim 5, wherein the adhesion is between leukocytes and endothelial cells in the presence of sickle red blood cells.

* * * * *